(12) United States Patent
Morgenstern

(10) Patent No.: US 8,722,012 B2
(45) Date of Patent: *May 13, 2014

(54) METHOD FOR PREVENTING NASOLACRIMAL DUCT OBSTRUCTION

(71) Applicant: Kenneth Eli Morgenstern, Wayne, PA (US)

(72) Inventor: Kenneth Eli Morgenstern, Wayne, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/962,509

(22) Filed: Aug. 8, 2013

(65) Prior Publication Data
US 2013/0323327 A1 Dec. 5, 2013

Related U.S. Application Data

(63) Continuation of application No. 12/012,469, filed on Feb. 4, 2008, now Pat. No. 8,529,871, which is a continuation of application No. 11/112,553, filed on Apr. 25, 2005, now abandoned.

(51) Int. Cl.
| | | |
|---|---|---|
| *A61K 51/00* | (2006.01) | |
| *A61M 36/14* | (2006.01) | |
| *A61K 9/00* | (2006.01) | |
| *A61K 38/00* | (2006.01) | |
| *A61K 47/00* | (2006.01) | |
| *A61P 9/10* | (2006.01) | |
| *A61P 27/02* | (2006.01) | |
| *A61K 9/06* | (2006.01) | |
| *A61K 9/08* | (2006.01) | |
| *A61K 47/02* | (2006.01) | |

(52) U.S. Cl.
CPC ............ *A61K 9/0048* (2013.01); *A61K 9/06* (2013.01); *A61K 9/08* (2013.01); *A61K 47/02* (2013.01)

USPC .............. 424/1.11; 514/1.2; 514/20.8

(58) Field of Classification Search
USPC ........................................... 424/1.11
See application file for complete search history.

(56) References Cited

U.S. PATENT DOCUMENTS

| | | | |
|---|---|---|---|
| 6,803,199 B2 | 10/2004 | Carrasco et al. | |
| 8,529,871 B2 * | 9/2013 | Morgenstern | 424/1.11 |
| 2004/0191332 A1 | 9/2004 | Chang et al. | |
| 2006/0193832 A1 | 8/2006 | Domann, Jr. et al. | |

OTHER PUBLICATIONS

Kloos et al., "Nasolacrimal Drainage System Obstruction from Radioactive Iodine Therapy for Thyroid Carcinoma," Journal of Clinical Endocrinology & Metabolism (2002) 87(12):5817-5820.
Burns et al., "Nasolacrimal Obstruction Secondary to I131 Therapy," Ophthalmic Plastic & Reconstructive Surgery (2004) 20(2):126-129.
Gennaro, Alfonso, "Ophthalmic Preparations," Remington's Pharmaceutical Sciences 18th Edition (1990) pp. 1581-1595.
Amdur et al., "Essentials of Thyroid Cancer Management," Springer, 5D.2. Potential Side Effects and Complications of I-131 Therapy (2005) pp. 267-279.
German et al., "Reliability of drop size from multi-dose eye drop bottles: is it cause for concern," Eye (1999) 33:93-100.

* cited by examiner

*Primary Examiner* — Michael G Hartley
*Assistant Examiner* — Melissa Perreira
(74) *Attorney, Agent, or Firm* — Volpe and Koenig, P.C.

(57) ABSTRACT

The invention is directed to a method for preventing nasolacrimal duct obstruction (NLDO) in a patient receiving high dose radioactive iodine for treatment of cancer. The method includes administering an effective amount of perchlorate anion to the eyes of the patient.

19 Claims, 1 Drawing Sheet

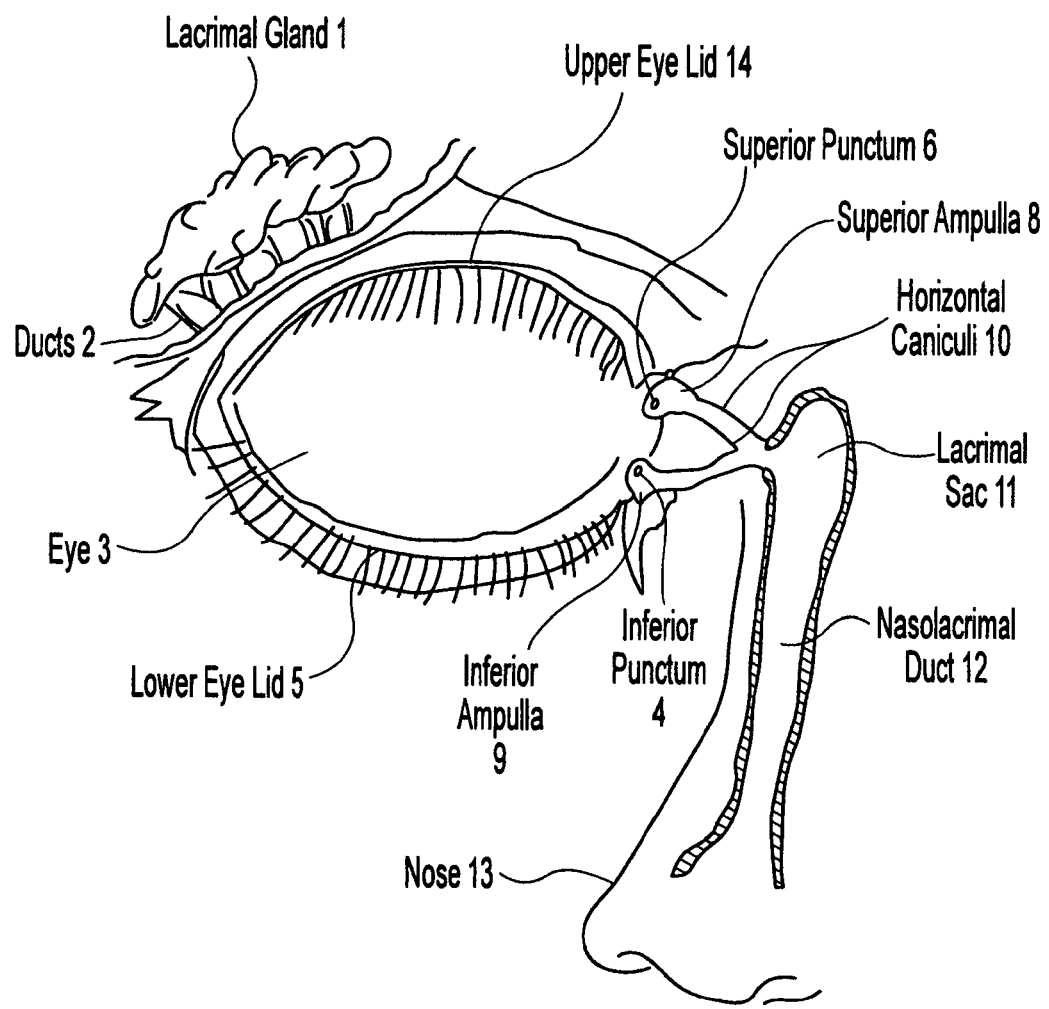

METHOD FOR PREVENTING NASOLACRIMAL DUCT OBSTRUCTION

BACKGROUND OF THE INVENTION

This application is a continuation of U.S. patent application Ser. No. 12/012,469, filed Feb. 4, 2008, which is a continuation of U.S. patent application Ser. No. 11/112,553, filed Apr. 25, 2005, both of which are incorporated herein by reference as if fully set forth.

A. FIELD OF THE INVENTION

The invention relates the prevention of radiation injury to tissues expressing the protein sodium/iodide symporter (NIS) and especially to radiation injury to the lacrimal sac and nasolacrimal duct in cancer patients being treated with high dose radioactive iodine.

B. Description of the Related Art

The sodium-iodide symporter is an integral membrane protein that resides in the basolateral membrane of epithelial cells located in such organs as the thyroid. The sodium-iodide symporter cannot distinguish between normal and radioactive iodide, thus providing a useful exploit for diagnosis and treatment of certain thyroid disease. Small amounts of radioactive iodine ($I^{123}$) injected into patients are rapidly concentrated in the thyroid, providing a means to image the thyroid for detection of tumors and other abnormalities. Administration of radioiodine ($I^{131}$) is widely used for treatment of hyperthyroidism and some types of thyroid cancer; in this case the radioactivity is concentrated rather precisely in the tissue requiring destruction.

The sodium-iodide symporter simultaneously transports both Na+ and I− ions from extracellular fluid (i.e. blood) into the thyroid epithelial cell. This process is an example of secondard active transport. Energy is provided by the electrochemical gradient of sodium across the cell membrane; the low intracellular concentration of sodium is maintained by sodium pumps. Although, the sodium-iodide symporter is most highly expressed in thyroid epithelial cells, lower levels of expression can be detected in mammary gland, salivary gland, stomach and colon tissue. See U.S. Pat. No. 6,803,199, Col. 1 and 2.

Ophthalmic complications following $I^{131}$ radiation therapy have been observed in a significant percentage of patients being treated for thyroid cancer. Symptoms such as ocular dryness, epiphora (watering of the eyes due to obstruction of the lacrimal passages), dry mouth (xerostomia) and nasolacrimal duct obstruction (NLDO) have been observed. Kloos et al, J Clin Endocrinol Metab. 2002 Dec; 87(12): 5817-20 and Burns et al, Opthal Plast Reconstr Surg. 2004 Mar; 20 (2): 126-9.

It is believed that the cases of NLDO observed in some patients receiving high dose radioiodine treatment is due to the concentration of radioactivity by the sodium-iodide symporter. High levels of radioactivity concentrated by NIS in a relatively small area in the lacrimal sac and nasolacrimal duct causes fibrosis which results in blockage in the lacrimal duct and nasolacrimal sac. It is also believed that some cases of dry mouth observed in patients being treated with high does radioiodine for head and neck cancers is due to accumulation of radioactivity in the salivary glands leading to fibrosis which blocks release of the salivary fluids.

The incidence of newly diagnosed head and neck cancers (excluding skin cancers) in the US is estimated at more than 50,000 cases annually. The most common type of cancer in the head and neck is squamous cell carcinoma, which arises in the cells that line the inside of the nose, mouth, and throat. Other less common types of head and neck cancers include salivary gland tumors, lymphomas and sarcomas. In addition to head and neck cancers, there are over 15,000 new cases of thyroid cancer each year in the United States.

Thyroid cancer is typically treated with surgery followed by radiation therapy. The three main types of treatment for managing head and neck cancer are radiation therapy, surgery and chemotherapy with the primary treatment being radiation therapy or surgery, or both combined.

In addition to being used in the treatment of head and neck and thyroid cancers, radioactive iodine ($I^{131}$) is widely used to treat hyperthyroidism. Hyperthyroidism results from excess quantities of thyroid hormone within the body. Rather than being classified as a specific disease, it is classified as a syndrome that describes the characteristics resulting from this condition. The causes of hyperthyroidism include Graves' disease; tumors of the thyroid gland, pituitary gland, testes or ovaries; inflammation of the thyroid from a viral infection or other inflammation; ingestion of excessive amounts of thyroid hormone; and ingestion of excessive iodine. Graves' disease accounts for 85% of all cases of hyperthyroidism. The incidence is 1 out of 1,000 people.

Finally, doctors are increasingly using radioiodine to treat breast cancer. Radioactive $I^{131}$ is given either orally or by injection. Using $I^{131}$, the clinician is able to selectively target the cancerous breast tissue as opposed to normal breast tissue. The reason for this is that although normal breast tissue has some expression of NIS, cancerous breast tissue expresses the protein at higher amounts. The result is by treating patients with $I^{131}$ the cancerous breast tissue will receive more amounts of the radioactivity then the surrounding normal tissue. By controlling the amount of $I^{131}$ given to the patient, it may be possible to keep the level of toxicity to the normal tissue low while reaching high enough levels in the cancerous tissue to destroy the cancerous tissue.

In the United States each year, as many as 100,000 people may be treated with high dose $I^{131}$. This number is expected to increase as the use of $I^{131}$ to treat breast cancer because more common. With the increased use of high dose radioiodine, it is expected that the incidence of NLDO will increase as well.

The traditional procedure most often relied on for relief of NLDO is incisional dacryocystorhinostomy (DCR). This procedure has a number of drawbacks: recovery time is significant, an incisional scar may develop due to invasive procedures, there is potential for excess bleeding, the procedure must be done under anesthesia usually general anesthesia, and the costs associated with the surgical procedure are not trivial. The DCR procedure has a high success rate in patients suffering from NLDO caused by other than high dose radioiodine; however, in patients where the nasolacrimal duct is obstructed as a result of receiving high dose radioiodine, the DCR procedure does not work very well.

Currently, there is not available a safe and effective method for preventing the fibrosis that can occur in the nasolacrimal duct area due to the administration of high dose radioiodine. A method that prevents or reduces the formation of fibrosis in the nasolacrimal duct rather than treats fibrosis after it forms, is highly desirable, The method of the invention described herein avoids all of the drawbacks associated with DCR. It is a cost effective, safe, non-invasive method that utilizes topical application of perchlorate anion in ophthalmic solutions, ophthalmic creams or gels to block the ability of the sodium-iodide symporter to concentrate radioactivity. The method of the invention is so safe and effective and cost effective that it should be the standard of care for every patient receiving high does $I^{131}$ therapy for treatment of cancer and especially for treatment of head and neck, thyroid and breast cancers.

SUMMARY OF THE INVENTION

The invention is directed to a method for preventing nasolacrimal duct obstruction (NLDO) in a patient receiving high dose radioactive iodine for treatment of cancer, especially for treatment of thyroid, head and neck and breast cancers which comprises administering to the eyes of said patient an effective amount of perchlorate anion.

BRIEF DESCRIPTION OF THE DRAWING

FIG. 1 is a simplified representation of the nasolacrimal system anatomy. Tears are produced in the lacrimal gland 1, flow through ducts 2 leading to the surface of the eyeball 3 and spread over the surface of the eyeball 3. When one blinks the upper and lower eyelids 4 and 5 push the tears which also contain proteins and sugars to the inside corner of the eye. There are two openings at the inside corner of each eye near the nose, the superior puncta 6 and inferior puncta 7 which open into the vertical caniculi 8. The vertical caniculi 8 bend at right angles at the superior ampulla 9 and inferior ampulla 10 and form the horizontal caniculi 11. The horizontal caniculi 11 drain tears and other fluids into the lacrimal sac 11 which is connected with the nasolacrimal duct 12 and which opens into the nose 13.

DETAILED DESCRIPTION OF THE INVENTION

The invention is directed to a method for preventing nasolacrimal duct obstruction (NLDO) in a patient receiving radioactive iodine and especially high dose radioactive iodine for treatment of cancer which comprises administering to each eye of said patient an effective amount of perchlorate anion.

A further embodiment of the invention is directed to a method for preventing nasolacrimal duct obstruction (NLDO) in a patient receiving high dose radioactive iodine ($I^{131}$) treatment for thyroid, head and neck and breast cancer which comprises administering to each eye of said patient an effective amount of perchlorate anion, wherein the patient is pre-treated with perchlorate anion for a period of from about 3 to about 5 days prior to initiation of high dose $I^{131}$ therapy, wherein treatment with perchlorate anion continues for as long as the patient receives high dose radiation therapy, and wherein treatment with perchlorate anion is continued for from about 3 to about 5 days after cessation of radiation therapy.

The term "nasolacrimal duct obstruction" (NLDO) as used herein to refers to a blockage in the distal horizontal caniculi 10, lacrimal sac 11 and/or the nasolacrimal duct 12 which prevents liquid from draining into the nose. As a result of the blockage there is a buildup of tears, containing mucin, sugars and other components such as bacteria in the areas just described leading to irritation and infection.

Symptoms of NLDO are epiphora (excessive tearing) due to a decrease in tear draining, inflammation and infection (dacryocystitis) of the lacrimal sac. The area beneath the eyes next to the nose can become red, inflamed, and sensitive to the touch. The area usually is swollen, and there may be a mucous discharge from the opening of the nasal corner of the eye. Common complaints include itching, irritation, burning, redness, conjunctivitis and pain.

As used herein the term "high dose" radioactive iodine (RAI) refers to cumulative doses of radioactive iodine ($I^{131}$) of about 150 mCi or greater. Although, iodine can be made into two radioactive isotopes for medical uses: $I^{123}$ and $I^{131}$, the radiation that $I^{123}$ gives off is generally used in scanning or imaging rather than for treatment. The RAI that is most often used in chemotherapy is $I^{131}$. It is usually administered to the patient by mouth either as a capsule or a liquid or intravenously (IV). RAI that is not concentrated in tissue is eliminated from the body through sweat and urine.

The term "perchlorate anion (ClO4-)" as used herein refers to the anion that is produced when solid salts of ammonium, potassium, and sodium perchlorate, and perchloric acid are dissolved in an aqueous liquid.

The term "effective amount" is used herein to mean an amount of perchlorate anion sufficient to reduce or inhibit fibrosis in the distal caniculi, lacrimal sac and/or nasolacrimal duct caused by the concentration of radioactivity by the NIS protein in a patient receiving radioiodine therapy. Any source of perchlorate ion may be used in the method of the invention. However, potassium perchlorate and sodium perchlorate are preferred for use in the methods of the invention because they are in use in other approved pharmaceutical applications and pharmaceutical grade (USP) compound is readily available. Administration of perchlorate anion to the patient should be started from about 3 to 5 days prior to the initiation of $I^{131}$ chemotherapy and should continue during the course of chemotherapy and for 3 to 5 days after cessation of $I^{131}$ therapy.

Preferred for use in the method of the invention are ophthalmic medicaments containing from about 10 mg/ml to about 500 mg/ml of potassium perchlorate ($KClO_4$) or sodium perchlorate ($NaClO_4$) and preferably from about 40 mg/ml to about 400 mg/ml and more preferably from about 50 mg/ml to from about 100 mg/ml.

The ophthalmic medicament containing the perchlorate anion is topically administered in the corner of the eye near the superior and inferior puncta 6 and 7. The perchlorate anion may be administered topically to the eye as for example a sterile liquid e.g., an eye wash or eye drops, an aqueous gel, or ophthalmic ointment or cream. As would be recognized by one skilled in this art, any ophthalmic formulation that is sterile and that is pharmaceutically acceptable, i.e., is safe and effective for its intended purpose may be used to deliver perchlorate anion to the lacrimal sac and nasolacrimal duct.

The maximum volume of the lacrimal sac is about 30 µl. The average volume of a human tear is 7 µl. Most commercially eye drops have a per drop volume in the range of from 50-75 µl. If the droplet volume is much excess of 75 µl it probably will not get into the lacrimal sac and thus, the nasolacrimal duct, and the excess solution will be wasted as it drips out of the eye and down the face. Ideally, an eye drop solution will have a high concentration of drug in a minimum drop volume. Multiple drops administered at intervals, produces higher drug concentrations in the lacrimal sac and nasolacrimal duct.

An alternative to a solution of perchlorate anion for use in the methods of the invention is an ophthalmic ointment containing the perchlorate anion. An advantage of an ointment is that it has a longer contact time with the eye and potentially greater total drug bioavailability. Since an ointment can interfere with vision it is best used at bedtime. The perchlorate is added to the ointment base as a solution or a micronized powder. Most ophthalmic ointments are prepared with a base of white petrolatum and mineral oil, often with anhydrous lanolin. Some contain a polyethylene-mineral oil gel. Whatever base is used, it must be nonirritating to the eye, permit diffusion of the drug throughout the eye and retain activity of the perchlorate for a reasonable period of time upon storage.

The ophthalmic medicament containing perchlorate anion may be self administered or it may be administered by the clinician, in which case it may be instilled directly into the lacrimal sac and nasolacrimal duct.

As would be recognized by one skilled in this art, it is within the skill of the art to prepare sterile, shelf-stable ophthalmic solutions, gels and ointments. See for example, Remington's Pharmaceutical Sciences 18$^{th}$ Ed., Alfonso Gennaro Editor, 1990, Mack Publishing C., Easton, PA 18042, pp. 1581-1595 (now known as Remington: The Science and Practice of Pharmacy, 20th Edition, Alfonso Gennaro Editor, Lippincott Williams & Wilkins, Baltimore, Md.) for information regarding the properties of, and the preparation of, ophthalmic solutions and ointments.

Both potassium perchlorate and sodium perchlorate are in use to minimize or reduce accumulation of technetium or $I^{123}$ in certain tissues in patients undergoing imaging studies. Potassium perchlorate is available from Mallinckrodt Inc. St. Louis, Mo. 63134 under the trade name Perchloracap®. Perchloracap is supplied for use during diagnostic studies as an opaque gray gelatin capsule for oral administration. Each capsule contains 200 milligrams of potassium perchlorate ($KCIO_4$) mixed with an inert filler. Perchloracap is administered to minimize the accumulation of pertechnetate Tc 99$m$ in the choroid plexus and in the salivary and thyroid glands in patients receiving sodium pertechnetate Tc 99$m$ injection for brain and blood pool imaging and placenta localization.

Sodium perchlorate is manufactured in the United Kingdom by Torbay PMU, a division of the South Devon Healthcare Trust and is available in the UK as a 20 mg/ml solution for injection. Sodium Perchlorate Injection is used as a thyroid blocking agent for patients unable to tolerate alternative oral thyroid blocking agents when undergoing studies with radioiodinated radiopharmaceuticals known to de-iodinate in vivo.

Although potassium and sodium perchlorate have been used to block accumulation of technetium 99$m$ and $I^{123}$ in the thyroid gland, choroid plexus, and salivary glands there is no recognition in the art that perchlorate may reduce or eliminate fibrosis that can occur in the nasolacrimal area in patients receiving high dose radioiodine for treatment of various cancers.

The invention and the manner and process of making and using it are now described in such full, clear, and concise terms as to enable any person skilled in the art to which it pertains to make and use same. It is to be understood that the forgoing describes preferred embodiments of the present invention and that modifications may be made therein without departing from the spirit or scope of the present invention as set forth in the claims. To particularly point out and distinctly claim the subject matter regarded as the invention, the following claims conclude this specification.

What is claimed is:

1. A method for preventing nasolacrimal duct obstruction that may occur upon high dose radioactive iodine treatment in a patient receiving high dose radioactive iodine for treatment of cancer, the method comprising topically administering to the eyes of said patient a therapeutically effective amount of perchlorate anion.

2. The method according to claim 1 wherein said radioactive iodine is $I^{131}$.

3. The method according to claim 2 wherein the cumulative dose of $I^{131}$ given to the patient is greater than 150 mCi.

4. The method according to claim 2 wherein the source of said perchlorate anion is a compound selected from the group comprising potassium perchlorate, sodium perchlorate, ammonium perchlorate and perchloric acid.

5. The method according to claim 2 wherein said perchlorate anion is administered to the eyes of said patient for from about 3 days to about 5 days prior to initiation of treatment with high dose radioactive iodine and wherein said perchlorate anion treatment is continued for as long as said patient receives high dose radioactive iodine and wherein said perchlorate anion is administered to the eyes of said patient for from about 3 days to from about 5 days after high dose radioactive iodine treatment is discontinued.

6. The method according to claim 1 wherein said perchlorate anion is administered to the eyes of said patient as a topical liquid, gel, cream or ointment.

7. The method according to claim 3 wherein said cancer is selected from the group consisting of head and neck cancer, thyroid cancer and breast cancer.

8. A method for preventing nasolacrimal duct obstruction that may occur upon high dose $I^{131}$ treatment in a patient receiving high dose $I^{131}$ radiation therapy for treatment of cancer, the method comprising topically administering to the eyes of said patient an effective amount of perchlorate anion in a volume of 75 μl or less per administration.

9. The method according to claim 8, wherein the patient is pre-treated with perchlorate anion for a period of from about 3 to about 5 days prior to initiation of the high dose $I^{131}$ radiation therapy.

10. The method according to claim 8, wherein treatment with perchlorate anion continues for as long as the patient receives high dose radiation therapy, and wherein treatment with perchlorate anion is continued for from about 3 to about 5 days after discontinuing the high dose $I^{131}$ radiation therapy.

11. The method according to claim 8 wherein the source of said perchlorate anion is a compound selected from the group comprising potassium perchlorate, sodium perchlorate, ammonium perchlorate and perchloric acid.

12. The method according to claim 11 wherein said perchlorate compound is administered at a dosage of from about 10 mg/ml to about 500 mg/ml.

13. The method according to claim 12 wherein said dosage is from about 40 mg/ml to about 400 mg/day.

14. The method according to claim 13 wherein said dosage is from about 50 mg/ml to about 100 mg/ml.

15. The method according to claim 8 wherein said cancer is selected from the group consisting of thyroid cancer, head and neck cancer and breast cancer.

16. The method according to claim 8 wherein said perchlorate anion is administered to the eyes as a topical liquid, gel, cream or ointment.

17. The method according to claim 16 wherein said topical liquid or gel is administered to the eyes as an aqueous liquid or aqueous gel.

18. The method according to claim 8 wherein said radioactive iodine is $I^{131}$ and is administered at a cumulative dosage of 150 mCi or greater.

19. The method according to claim 18 wherein said topical liquid or gel is administered to the eyes as an aqueous liquid or aqueous gel.

* * * * *